United States Patent
Loescher et al.

(10) Patent No.: US 7,189,887 B2
(45) Date of Patent: Mar. 13, 2007

(54) PROCESS FOR REMOVING NAPHTHALENE FROM ALKYLAROMATICS

(75) Inventors: Mitchell E. Loescher, Houston, TX (US); Christopher C. Boyer, Houston, TX (US); Michael J. Keenan, Baton Rouge, LA (US); Steven E. Silverberg, Baytown, TX (US)

(73) Assignees: Catalytic Distillation Technologies, Pasadena, TX (US); ExxonMobil Chemical Patents, Inc., Baytown, TX (US)

( * ) Notice: Subject to any disclaimer, the term of this patent is extended or adjusted under 35 U.S.C. 154(b) by 145 days.

(21) Appl. No.: 11/010,990

(22) Filed: Dec. 13, 2004

(65) Prior Publication Data

US 2006/0129017 A1    Jun. 15, 2006

(51) Int. Cl.
*C07C 6/00*    (2006.01)
(52) U.S. Cl. .................. 585/475; 203/DIG. 6
(58) Field of Classification Search ............... 585/475; 203/DIG. 6
See application file for complete search history.

(56) References Cited

U.S. PATENT DOCUMENTS

| | | | |
|---|---|---|---|
| 5,055,627 A | 10/1991 | Smith, Jr. et al. | 585/467 |
| 5,243,115 A | 9/1993 | Smith, Jr. et al. | 585/446 |
| 5,446,223 A | 8/1995 | Smith, Jr. | 585/313 |
| 5,670,704 A | 9/1997 | Hagen et al. | 585/471 |
| 5,844,064 A | 12/1998 | Motoyuki et al. | 528/272 |
| 5,866,736 A | 2/1999 | Chen | 585/323 |
| 6,013,848 A | 1/2000 | Chen et al. | 585/323 |
| 6,111,157 A * | 8/2000 | Hendriksen et al. | 585/467 |
| 6,204,422 B1 | 3/2001 | Tsutsui et al. | 585/321 |
| 6,232,517 B1 | 5/2001 | Pazzucconi et al. | 585/481 |
| 2004/0006251 A1 * | 1/2004 | Schlosberg et al. | 585/475 |

* cited by examiner

*Primary Examiner*—Thuan Dinh Dang
(74) *Attorney, Agent, or Firm*—Kenneth H. Johnson

(57) ABSTRACT

A process for the reduction of naphthalene in process streams containing alkylaromatic solvents. Naphthalene is contacted with alkylbenzenes in a distillation column reactor in the presence of transalkylation catalyst to produce alkylnaphthalenes which are concurrently separated by fractional distillation as bottoms and the alkylbenzenes are separated as overheads.

20 Claims, 1 Drawing Sheet

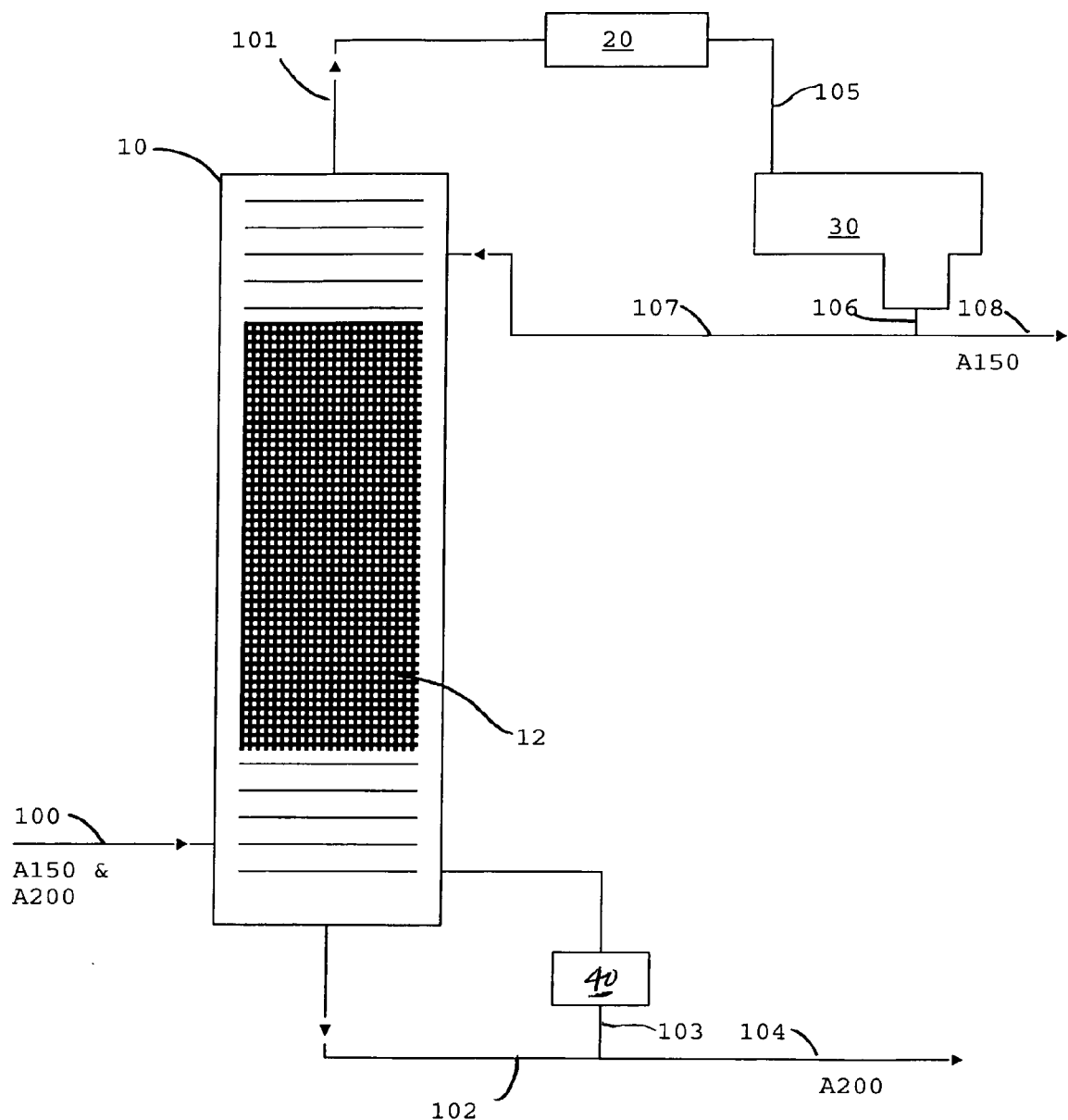

PROCESS FOR REMOVING NAPHTHALENE FROM ALKYLAROMATICS

BACKGROUND OF THE INVENTION

1. Field of the Invention

The present invention relates to a process for the removal of naphthalene from a hydrocarbon stream carried out concurrently with fractional distillation within a distillation column reactor. More particularly the invention relates to a process wherein the naphthalene is converted to alkylnaphthalenes by transalkylation with alkylbenzenes. More particularly the invention relates to the conversion of naphthalene contained in aromatic solvents to alkylnaphthalenes by transalkylating the naphthalene in the aromatic solvent with alkylbenzenes contained within the solvent.

2. Related Information

Alkylbenzenes, naphthalene, and alkylnaphthalenes are produced as a by-product in olefin plants, fluid catalytic crackers, catalytic reformers and coal tar plants. Dialkylbenzenes have value as precursors of monomers for high performance polymers. Mixtures of alkylbenzenes and alkylnaphthalenes have found value as solvents.

The terms A150 and A200 have been applied in the industry to aromatic solvents produced by the separation of heavy boiling compounds from the effluent of gasoline catalytic reforming units and olefin plants. A150 and A200 are distilled in such a way as to afford flash points of 150° F. and 200° F., respectively. The heavier solvent contains significant amounts of naphthalene. Naphthalene has been identified as a carcinogen causing cancer, haemolytic anaemia (damage to red blood cells), and local respiratory tract irritation (nose and throat). It has therefore become desirable to remove naphthalene from these solvents.

U.S. Pat. Nos. 6,232,517 and 5,670,704 describe the chemistry for alkylating naphthalene in the presence of a solid catalyst to selectively yield 2,6 dimethylnaphthalene. U.S. Pat. Nos. 6,204,422, and 5,844,064 describe a chemistry wherein alkylnaphthalenes are produced by transalkylation over a catalyst. Finally U.S. Pat. No. 5,243,115 discloses a process whereby aromatic compounds are alkylated with an olefin, such as ethylene or propylene, in a distillation column reactor.

SUMMARY OF THE INVENTION

The process for the removal of naphthalene from mixtures comprising naphthalene and alkylbenzenes utilizes a distillation column reactor to transfer alkyl groups from alkylbenzenes to naphthalene by transalkylation and simultaneously separating the alkylbenzenes from the alkylnaphthalenes produced in the transalkylation. The process can be simply described as comprising the steps of:

(a) feeding a stream containing naphthalene and alkylbenzenes to a distillation column reactor containing a bed of transalkylation catalyst;

(b) concurrently in said distillation column reactor,
  (i) contacting the naphthalene with the alkylbenzenes in the presence of the transalkylation catalyst under conditions to transalkylate a portion of the naphthalene to form a reaction mixture containing alkyl naphthalene, alkyl benzenes and unreacted naphthalene, and
  (ii) separating the unreacted alkylbenzenes from the unreacted naphthalene and alkyl naphthalene by fractional distillation; whereby (c) alkylbenzenes are withdrawn from said distillation column reactor as overheads; and (d) alkylnaphthalenes are withdrawn from said distillation column reactor as bottoms.

Preferably the process is operated under conditions whereby the naphthalene is trapped in the catalyst zone. Naphthalene is heavier (higher boiling) than the overhead fraction and lighter (lower boiling) than the bottoms fraction. Alkylbenzenes exit in the overheads of the column while alkylnaphthalenes exit in the bottoms of the column.

BRIEF DESCRIPTION OF THE DRAWING

The FIGURE is a flow diagram in schematic form of the preferred embodiment of the invention.

DETAILED DESCRIPTION OF THE PREFERRED EMBODIMENT

In the current invention a mixed stream of alkylbenzenes, naphthalene and alkylnaphthalenes is fed into a distillation column reactor below a catalyst zone.

Naphthalene has a boiling point between the alkylbenzenes and alkylnaphthalenes components. The distillation tower is designed with enough stages and operates with enough reflux such that the bottom of the tower operates at the boiling point of the alkylnaphthalenes and the top of the tower operates at the boiling point of the alkylbenzenes. Naphthalene is too light to exit the bottom of the tower and too heavy to exit the top of the tower, so it accumulates in the catalyst zone until it is converted to alkylnaphthalenes.

The column pressure is set such that the column temperature allows for a reasonable rate of reaction for alkylation or transalkylation, between 5 and 100 psia, preferably 30 psia (about 15 psig). The feed point is below the catalyst bed so that heavy materials and impurities that may poison the catalyst exit the bottom of the tower without reaching the catalyst zone.

The catalysts used in the transalkylation process are those catalysts generally known as aromatic alkylation catalysts, such as metal oxides, supported metal oxides, solid acid resins or zeolites. The most preferred catalysts are molecular sieves.

Molecular sieves are porous crystalline, three-dimensional alumina-silicates of the zeolite mineral group. The crystal skeleton is composed of silicon and aluminum atoms each surrounded by four oxygen atoms to form a small pyramid or tetrahedron (tetrahedral coordination). The term molecular sieve can be applied to both naturally occurring zeolites and synthetic zeolites. Naturally occurring zeolites have irregular pore size and are not generally considered as equivalent to synthetic zeolites. In the present invention, however, naturally occurring zeolites are acceptable so long as they are substantially pure. The balance of the present discussion shall be directed to the synthetic zeolites with the understanding that natural zeolites are considered equivalent thereto as indicated above, i.e., insofar as the natural zeolites are the functional equivalents to the synthetic zeolites.

Usually synthetic zeolites are prepared in the sodium form, that is, with a sodium cation in close proximity to each aluminum tetrahedron and balancing its charge. To date four principal types of molecular sieves have been reported, A, X, Y and L erionite, omega, beta and mordenite. The A types have relative small pore size. By the term pore size is meant the effective pore size (diameter) rather than the free pore size (diameter). Types X and Y have larger pore size (approximately 10 Å.) and differ as to the range of ratio of $Al_2O_3$ to $SiO_2$ as:

| Type X | $Al_2O_3/2.0$–$3.0$ $SiO_2$ |
|---|---|
| Type Y | $Al_2O_3/3.0$–$6.0$ $SiO_2$ |

Types L, beta and other types listed have still higher ratios of $SiO_2$ to $Al_2O_3$.

The mole sieve catalysts employed in the present invention are the acid form mole sieves or exhibit acidic characteristics. The acid form of the mole sieves is commercially available but also may be prepared by treating the mole sieves with acid to exchange Na for hydrogen. Another method to produce the acid form is to treat the mole sieve with decomposable cations (generally ammonium ions) to replace Na with the decomposable ions and thereafter to heat the mole sieve to decompose the cation leaving the acid form. Generally the Na form mole sieve is treated with soluble ammonium salts to remove the Na and thereafter the mole sieve is heated to a temperature of about 350° C. to remove the ammonia. The removal of $Na^+$ ions with $NH^+_4$ is more easily carried out than with multivalent ions as described below and these catalysts are generally more active, but less stable to heat than the multivalent cation exchange forms. Mole sieves, which have had their alkali metal reduced to low levels by partial treatment with $NH^+_4$ and partial multivalent metal cation exchange, possess increased activity and increased stability.

In addition to mole sieves which are acidic according to the Brönsted Theory, those mole sieves which exhibit acidic characteristics under the Lewis Theory, for example, calcium exchanged mole sieves are suitable for the present reaction. By exchanging the univalent cations (e.g. $Na^+$) with multivalent cation, strong ionic activity is imparted. The ratio of $SiO_2:Al_2O_3$, valence and radius of the cation and the extent of exchange all affect the catalyst activity. In general, activity increases with (1) increased $SiO_2:Al_2O_3$ ratio, (2) decreased cation radius and an increase in cation valence. The effect of replacing univalent ions (e.g. $Na^+$) with bivalent (e.g. $Ca^{++}$) is much greater than replacing the bivalent ions with cations of greater valence.

The various types of mole sieves having reduced alkali metal content are characterized as the acid form molecular sieve and are all contemplated as useful in the present invention.

For use in a catalytic distillation reaction system, the catalyst is preferably prepared in the form of a catalytic distillation structure. The catalytic distillation structure must be able to function as catalyst and as mass transfer medium. The catalyst must be suitably supported and spaced within the column to act as a catalytic distillation structure. The catalytic distillation process employs a catalyst system (See U.S. Pat. Nos. 5,730,843; 4,302,356; and 4,215,011) which provides for both reaction and distillation concurrently in the same reactor, at least in part within the catalyst system. The method involved is briefly described as one where concurrent reaction and distillation occur in combination reaction-distillation structures which are described in U.S. Pat. Nos. 4,242,530; 4,250,052; 4,232,177; 4,302,356; 4,307,254; and 4,336,407. Additionally U.S. Pat. Nos. 4,302,356 and 4,443,559 disclose catalyst structures which are useful as distillation structures.

In the present reaction, catalytic distillation is a benefit first, because the reaction is occurring concurrently with distillation, and the initial reaction products and other stream components are removed from the reaction zone as quickly as possible reducing the likelihood of side reactions. Second, because all the components are boiling, the temperature of reaction is controlled by the boiling point of the mixture at the system pressure. The heat of reaction simply creates more boil up but no increase in temperature at a given pressure. As a result, a great deal of control over the rate of reaction and distribution of products can be achieved by regulating the system pressure. Also, adjusting the throughput (residence time=liquid hourly space velocity$^{-1}$) gives further control of product distribution and to a degree control of the side reactions such as oligomerization. A further benefit that this reaction may gain from catalytic distillation is the washing effect that the internal reflux provides to the catalyst thereby reducing polymer build up and coking.

The temperature in the distillation column reactor is determined by the boiling point of the liquid mixture present at any given pressure. The temperature in the lower portions of the column will reflect the constitution of the material in that part of the column, which will be higher than the overhead; that is, at constant pressure a change in the temperature of the system indicates a change in the composition in the column. To change the temperature the pressure is changed. Temperature control in the reaction zone is thus effected by a change in pressure; by increasing the pressure, the temperature in the system is increased, and vice versa.

The reflux ratio, represented as external L/D (wt. liquid just below the catalyst bed/wt. distillate) in the instant invention has been found to be important and may beneficially range from 2 to 15. Increasing the reflux ratio increases the effective residence time of the naphthalene in the catalyst column which increases the conversion. The preferred reflux ratio is 6 or greater with a most preferred reflux ratio of greater than 10.

EXAMPLE 1

Referring now to the FIGURE a simplified flow diagram of the process is shown. A mixture of A150 and A200 having a ratio of 2:1 A150 to A200, the composition of which is shown in TABLE I, was fed via flow line 100 to distillation column reactor 10 containing a bed 12 of MCM-49 Zeolite as manufactured by Exxon Mobil Chemical Company. The naphthalene reacts with alkylbenzenes contained within the feed stream in the presence of the zeolite catalyst bed 12 to produce a reaction mixture containing alkylbenzenes, naphthalene, and alkylnaphthalenes. The alkylnaphthalenes are the highest boiling material in the column and are removed as bottoms along with the A200 product via flow line 102. A portion of the bottom stream is recycled through reboiler 40 via flow line 103 to provide heat. The A200 solvent product is removed via flow line 104.

The alkylbenzenes in the A150 product are the lowest boiling materials in the column and thus exit the top of the column as overheads via flow line 101 and passed to condenser 20 where the product is condensed and then passed on to reflux drum 30 via flow line 105. Liquid is removed from the reflux drum via flow line 106 with a portion being returned to the distillation column reactor 10 as reflux via flow line 107. A150 product is taken via flow line 108. By adjusting the reflux rate the naphthalene can be retained within the catalyst bed 12 until almost all of it is reacted. A small amount may exit with the overheads.

The operating conditions and results are shown in TABLE II. The temperature was maintained at about 530° F. in the bed. Otherwise the conditions are shown. A reflux ratio (external L/D) preferably over 6, more preferably over 10 provided the best conversion. In the preferred embodiment the product split should be adjusted such that the naphthalene concentration bulges in the middle of the catalyst bed. It was found that if the split were not adjusted properly the naphthalene would exit the top of the column (too much distillate) or out the bottom (too much bottoms) with a very low conversion. High naphthalene conversion was achieved when 45 to 70 wt % of the feed exited as distillate product.

If naphthalene were the only species affected by the reaction, a perfect split would have been 63 wt % distillate. It was found that the bottoms cut could be increased without obtaining light material in the product. Material balances suggest that additional species lighter than naphthalene were converted to the more desirable A200 product.

TABLE I

TYPICAL FEED

| Component | Wt. % |
|---|---|
| $C_6$ and lighter | 4.9165 |
| $C_7/C_9$ alkylbenzenes | 63.6982 |
| Naphthalene | 8.3323 |
| $C_{10}/C_{11}$ alkylbenzene | 9.0897 |
| 2 methylnaphthalene | 8.7272 |
| 1 methylnaphthalene | 4.5760 |
| biphenyl | 0.1412 |
| 2 ethylnaphthalene | 0.0000 |
| 1 ethylnaphthalene | 2.1850 |
| 2,6 dimethylnaphthalene | 0.9612 |
| 2,7 dimethylnaphthalene | 0.7982 |
| 1,7 & 1,3 dimethylnaphthalene | 1.9238 |
| 1,6 dimethylnaphthalene | 0.9858 |
| 1,5 dimethylnaphthalene | 0.7162 |
| 1,4 dimethylnaphthalene | 0.1874 |
| 1,3 dimethylnaphthalene | 0.4074 |
| 2 methyl biphenyl | 0.2916 |
| $C_{13}$ naphthalene | 1.5173 |
| methyl biphenyl | 0.3477 |
| other heavies | 0.1973 |

TABLE II

| RunHour | Pressure psig | Feed lb/hr | Distillate lb/hr | Reflux lb/hr | Reflux Ratio | Naph. Conv. wt % | Lights Conv. wt % |
|---|---|---|---|---|---|---|---|
| 384 | 15.4 | 0.54 | 0.43 | 2.28 | 5.28 | 83.1 | |
| 276 | 15.0 | 0.54 | 0.42 | 1.47 | 3.53 | 27.0 | |
| 300 | 15.0 | 0.54 | 0.33 | 1.30 | 3.88 | 50.5 | 6.7 |
| 456 | 15.0 | 0.59 | 0.31 | 3.74 | 12.06 | 99.1 | 33.0 |
| 348 | 15.0 | 0.59 | 0.43 | 2.18 | 5.08 | 66.0 | |
| 312 | 15.0 | 0.60 | 0.43 | 1.49 | 3.45 | 25.3 | |
| 168 | 15.0 | 0.60 | 0.31 | 1.25 | 4.02 | 56.5 | 25.2 |
| 444 | 15.0 | 0.60 | 0.34 | 4.01 | 11.73 | 98.9 | |
| 336 | 15.0 | 0.60 | 0.42 | 1.98 | 4.74 | 47.0 | |
| 228 | 15.0 | 0.60 | 0.40 | 1.42 | 3.57 | 32.6 | 4.4 |
| 372 | 15.0 | 0.60 | 0.34 | 2.21 | 6.55 | 81.8 | |
| 360 | 15.0 | 0.60 | 0.37 | 2.40 | 6.43 | 79.7 | |
| 216 | 15.0 | 0.61 | 0.31 | 2.32 | 7.48 | 98.2 | 28.0 |
| 192 | 15.0 | 0.61 | 0.38 | 1.53 | 4.06 | 31.0 | 15.5 |
| 432 | 15.0 | 0.61 | 0.36 | 3.95 | 11.01 | 97.4 | |
| 204 | 15.0 | 0.62 | 0.41 | 1.50 | 3.64 | 10.6 | |
| 480 | 15.0 | 0.62 | 0.31 | 3.90 | 12.58 | 99.5 | 38.1 |
| 468 | 15.0 | 0.62 | 0.35 | 3.81 | 10.80 | 99.1 | |
| 264 | 15.0 | 0.62 | 0.34 | 1.40 | 4.17 | 24.4 | |
| 252 | 15.0 | 0.62 | 0.45 | 1.30 | 2.90 | 6.1 | |
| 420 | 15.0 | 0.62 | 0.39 | 3.91 | 9.97 | 83.5 | |
| 240 | 15.0 | 0.65 | 0.33 | 1.40 | 4.20 | 40.5 | |
| 492 | 15.0 | 0.98 | 0.60 | 3.71 | 6.18 | 89.9 | 5.8 |
| 564 | 15.0 | 1.00 | 0.60 | 3.66 | 6.12 | 81.4 | 11.5 |
| 588 | 15.0 | 1.00 | 0.55 | 4.43 | 8.05 | 92.2 | 16.5 |
| 504 | 15.0 | 1.01 | 0.64 | 3.72 | 5.84 | 78.9 | 2.6 |
| 528 | 15.0 | 1.01 | 0.68 | 3.55 | 5.26 | 61.8 | 1.0 |
| 576 | 15.0 | 1.01 | 0.62 | 3.93 | 6.29 | 85.3 | 10.9 |
| 552 | 15.0 | 1.02 | 0.73 | 3.57 | 4.88 | 58.8 | |
| 600 | 15.0 | 1.91 | 1.12 | 4.34 | 3.89 | 66.8 | 13.3 |
| 612 | 15.0 | 1.99 | 1.21 | 4.37 | 3.61 | 59.4 | 7.8 |
| 624 | 15.3 | 2.04 | 1.16 | 4.19 | 3.60 | 52.2 | 10.3 |

The invention claimed is:

1. A process for the removal of naphthalene from mixtures comprising naphthalene and alkylbenzenes comprising the steps of:
   (a) feeding a stream containing naphthalene and alkylbenzenes to a distillation column reactor containing a bed of transalkylation catalyst;
   (b) concurrently in said distillation column reactor,
      (i) contacting the naphthalene with the alkylbenzenes in the presence of the transalkylation catalyst under conditions of pressure, temperature, and reflux rate to trap the naphthalene within the bed of transalkylation catalyst to transalkylate a portion of the naphthalene to form a reaction mixture containing alkyl naphthalene, alkyl benzenes and unreacted naphthalene, and
      (ii) separating the unreacted alkylbenzenes from the unreacted naphthalene and alkyl naphthalene by fractional distillation; whereby
   (c) alkylbenzenes are withdrawn from said distillation column reactor as overheads; and
   (d) alkylnaphthalenes are withdrawn from said distillation column reactor as bottoms.

2. The process according to claim 1 wherein said stream comprises naphthalene, alkylbenzenes and alkylnaphthalenes.

3. The process according to claim 1 wherein a portion of the overheads is condensed and returned to said distillation column reactor as reflux.

4. The process according to claim 1 wherein the pressure, temperatures, and reflux rate are controlled such that the naphthalene is maintained within the bed of transalkylation catalyst such that substantially all of the naphthalene is reacted with alkyl benzenes.

5. The process according to claim 1 wherein the ratio of liquid returned to said distillation column to distillate product is in the range of 2 to 15.

6. The process according to claim 5 wherein the ratio of liquid returned to said distillation column to distillate product is at least 6.0.

7. The process according to claim 1 wherein said transalkylation catalyst is a zeolite.

8. The process according to claim 1 wherein the pressure, temperatures and reflux rate are controlled such that the naphthalene is maintained within the bed of transalkylation catalyst such that substantially all of the naphthalene is reacted with alkyl benzenes.

9. The process according to claim 8 wherein the ratio of liquid returned to said distillation column to distillate product is in the range of 2 to 15.

10. The process according to claim 9 wherein the ratio of liquid returned to said distillation column to distillate product is at least 6.0.

11. The process according to claim 10 wherein said transalkylation catalyst is a zeolite.

12. The process according to claim 11 wherein said stream containing naphthalene and alkyl benzenes comprises a mixture of A150 and A200 aromatic solvents.

13. The process according to claim 12 wherein said overheads comprise A150 aromatic solvent having a reduced naphthalene content and said bottoms comprise A200 aromatic solvent having a reduced naphthalene content.

14. The process according to claim 13 wherein the ratio of A150 to A200 aromatic solvent in said stream is 2:1 and the total naphthalene content of said stream is about 8 percent.

15. A process for the removal of naphthalene from mixtures comprising naphthalene and alkylbenzenes comprising the steps of:
(a) feeding a stream containing naphthalene and alkylbenzenes to a distillation column reactor containing a bed of transalkylation catalyst;
(b) concurrently in said distillation column reactor,
 (i) contacting the naphthalene with the alkylbenzenes in the presence of the transalkylation catalyst under conditions of pressure, temperature, and reflux rate to trap the naphthalene within the bed of transalkylation catalyst to transalkylate a portion of the naphthalene to form a reaction mixture containing alkyl naphthalene, alkyl benzenes and unreacted naphthalene, and
 (ii) separating the unreacted alkylbenzenes from the unreacted naphthalene and alkyl naphthalene by fractional distillation; whereby
(c) alkylbenzenes are withdrawn from said distillation column reactor as overheads;
(d) alkylnaphthalenes are withdrawn from said distillation column reactor as bottoms; and
(e) naphthalene is maintained within the bed of alkylation transalkylation catalyst.

16. The process according to claim 15 wherein said stream comprises naphthalene, alkylbenzenes and alkylnaphthalenes.

17. The process according to claim 15 wherein the ratio of liquid returned to said distillation column to distillate product is in the range of 2 to 15.

18. The process according to claim 17 wherein the ratio of liquid returned to said distillation column to distillate product is at least 6.0.

19. The process according to claim 18 wherein said transalkylation catalyst is a zeolite.

20. The process according to claim 19 wherein said stream containing naphthalene and alkyl benzenes comprises a mixture of A150 and A200 aromatic solvents.

\* \* \* \* \*